US00PP22396P2

(12) United States Plant Patent
Egger

(10) Patent No.: US PP22,396 P2
(45) Date of Patent: Dec. 20, 2011

(54) ***HEUCHERELLA* PLANT NAMED 'BRASS LANTERN'**

(50) Latin Name: ***Heucherella* hybrid**
Varietal Denomination: Brass Lantern

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/806,930

(22) Filed: Aug. 23, 2010

(51) Int. Cl.
*A01H 5/00* (2006.01)

(52) U.S. Cl. ..... Plt./441

(58) Field of Classification Search ..... Plt./441
See application file for complete search history.

*Primary Examiner* — Annette Para
(74) *Attorney, Agent, or Firm* — Klarquist Sparkman, LLP

(57) ABSTRACT

A new and distinct *Heucherella* plant substantially as shown and described, characterized by brassy gold and red spring leaves, glossy leaves, olive green and brown summer leaves, large, distinctive, palmately lobed leaves, large plant size, and excellent vigor.

1 Drawing Sheet

Botanical denomination: *Heucherella* hybrid.

Variety designation: 'Brass Lantern'.

Cross reference to *Heucherella* 'Sweet Tea' (U.S. Plant Pat. No. 21,296).

The present invention relates to a new and distinct cultivar of *Heucherella* and given the cultivar name of 'Brass Lantern'. *Heucherella* is in the family Saxifragaceae. *Heucherella* 'Brass Lantern' originated from a controlled cross between *Heuchera* 'V3' (a proprietary unreleased *Heuchera villosa* hybrid), as the seed parent, and massed selected *Tiarella*, as the pollen parent. The offspring were extremely variable and interesting. This is the third selected variety.

Compared to the seed parent, *Heuchera* 'V3' (unpatented), the new variety has leaves that are deeply lobed rather than shallowly lobed and more orange in color with a red center along the vein compared to no blotch.

Compared to the pollen parent, one of a *Tiarella* mass, the new variety has brassy gold and red foliage in spring rather than green.

Compared to *Heucherella* 'Sweet Tea' (U.S. Plant Pat. No. 21,296), the new variety has glossy leaves rather than a matte finish and gold with red centered spring leaves rather than bright rose orange with maroon centers.

This new *Heucherella* is unique in its coloration. There are no other varieties of this coloration known to the breeder. It is distinguished by:

1. brassy gold and red spring leaves,
2. glossy leaves,
3. olive green and brown summer leaves,
4. large, distinctive, palmately lobed leaves,
5. large plant size,
6. and excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one-year-old *Heucherella* 'Brass Lantern' in bloom, growing in a garden in April in Portland, Oreg.

FIG. 2 shows a one-year-old *Heucherella* 'Brass Lantern' in the ground in the garden in August in Canby, Oreg.

DETAILED PLANT DESCRIPTION

The following is a detailed description of the new *Heucherella* cultivar based on observations of two-year-old specimens growing outside in the ground in the trial field in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5th edition.

Plant:

*Form.*—Basal rosette, herbaceous perennial.
*Hardiness.*—USDA Zone 4 to 9.
*Size.*—30 cm tall from top of the foliage to the ground and 43 cm wide.
*Habit.*—Mounding.
*Vigor.*—Excellent.
*Roots.*—Fibrous, freely branching, fine, and white in color; roots develop easily from cuttings.

Leaf:

*Type.*—Simple.
*Arrangement.*—Rosette.
*Shape.*—Broadly ovate.
*Lobing/division.*—5 main lobes with the terminal the longest, the bottom lobes with secondary lobes.
*Venation.*—Palmate.
*Margins.*—Broadly crenate.
*Apex.*—Mucronulate.
*Base.*—Cordate.

*Blade size.*—Variable, grows to 13 cm wide and 13 cm long.

*Surface texture.*—Both surfaces glandular.

*Petiole description.*—Grows to 22.5 cm long and 3 mm wide, glandular hairs, between Red Purple 70A and Greyed Purple 186C.

*Leaf color.*—Variable depending on light and temperature, the gold tones are most prevalent during cool temperatures; spring top side, Greyed Orange 166C to Greyed Orange 166B with red center Greyed Red 178A, spring bottom side, closest to Greyed Red 178A; summer, fall topside Greyed Brown 199A with blotch Greyed Orange 166A.

Inflorescence:

*Size.*—Grows to 3 cm wide and 13 cm long.

*Type.*—Raceme.

*Number of flowers per raceme.*—About 50.

*Number of racemes in first spring flush.*—About 60.

*Peduncle.*—30 to 39 cm tall, 5 mm wide at base, between Red Purple 70A and Greyed Purple 186C, glandular hairs, with 1 to 2 petiolate cauline leaves (ovate, blades 1.5 to 5.5 cm long and 1.5 to 5.8 cm wide with 3 to 5 lobes, blotched, crenate, mucronate, cordate, glandular hairs on both sides, Greyed Orange 166C with red center Greyed Red 178A).

*Pedicel.*—Variable, glandular, 1-2 mm long, Greyed Purple 184B.

*Bloom time.*—Mid April to June in Canby, Oreg., with sporadic rebloom.

*Lastingness.*—Each raceme blooms for about 2 weeks on the plant.

Flower bud:

*Size.*—2 mm wide and 3 mm long.

*Description.*—Glandular puberulent, ovoid, down facing.

*Color.*—White N155D tinted Greyed Red 178A.

Flower:

*Type.*—Perfect.

*Shape.*—Campanulate.

*Size.*—7 mm wide and 5 mm deep.

*Petal description.*—5 in number, each oblanceolate, 5 mm long and 1.5 mm wide, 0 to 3 incisions, tip acuminate, base attenuate, margin entire, glabrous on top side and sparsely glandular on bottom side, White NN155B on both sides.

*Calyx description.*—5 mm wide and 3 mm deep, with 5 lobes, divided ¾ way to the base, campanulate, glandular hairs on outside, glabrous inside, tip obtuse, margin entire, White NN155D on both sides except tips which are White N155C.

*Stamen description.*—5 in number, filaments 2.5 mm long White NN155D, anthers sterile, less than 1 mm, Greyed Orange 165B.

*Pistil description.*—One central two beaked pistil, 5 mm long, White 155C.

*Fragrance.*—None.

Fruit and seed: None

Disease and pest tolerance: No known resistance to rust, a common problem with light leaf type *Heucherella*. Excellent disease tolerance to powdery mildew. All *Heucherella* are susceptible to root weevils.

I claim:

1. A new and distinct *Heucherella* plant as herein illustrated and described.

* * * * *

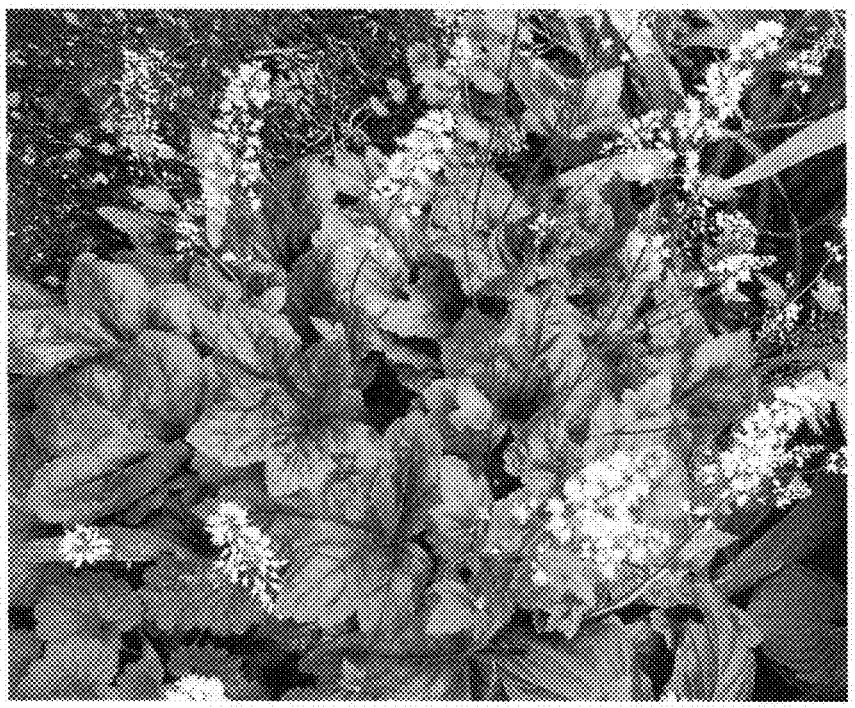

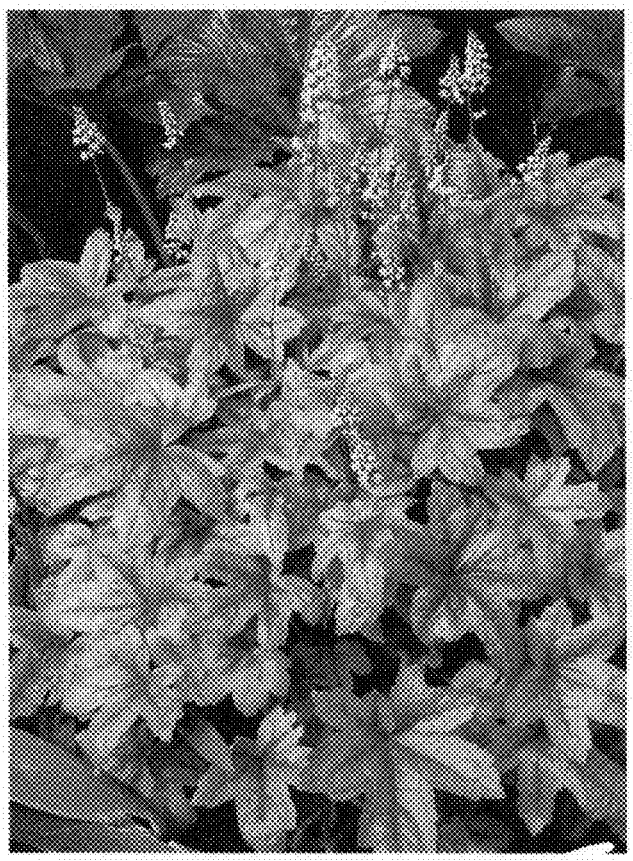
Figure 1 above. Figure 2 below.